United States Patent [19]

Magnasco et al.

[11] 4,228,801
[45] Oct. 21, 1980

[54] DILATOR FOR APPLICATION IN MEDICAL FIELD

[75] Inventors: Dante Magnasco, Bergamo; Livio Marinoni, Milan, both of Italy

[73] Assignee: Elektromedical Company S.r.l., Milan, Italy

[21] Appl. No.: 962,834

[22] Filed: Nov. 21, 1978

[30] Foreign Application Priority Data

Nov. 29, 1977 [IT] Italy ................................ 30190 A/77

[51] Int. Cl.³ ...................... A61M 29/02; A61M 25/00
[52] U.S. Cl. ............................... 128/344; 128/349 BV
[58] Field of Search .................... 128/344, 343, 349 B, 128/349 BV, 303.11, 303.12

[56] References Cited

U.S. PATENT DOCUMENTS

| | | | |
|---|---|---|---|
| 2,507,858 | 12/1950 | Kegel | 128/344 |
| 2,701,559 | 12/1955 | Cooper | 128/344 |
| 3,478,743 | 12/1969 | Ericson | 128/349 BV |
| 3,528,869 | 12/1970 | Dereniuk | 128/349 B |
| 3,799,173 | 3/1974 | Kamen | 128/349 B |
| 3,938,504 | 2/1976 | Dickinson et al. | 128/343 |
| 3,939,820 | 2/1976 | Grayzel | 128/344 |
| 4,085,757 | 4/1978 | Pevsner | 128/344 |
| 4,137,922 | 2/1979 | Leininger et al. | 129/344 |

Primary Examiner—Robert W. Michell
Assistant Examiner—C. W. Shedd
Attorney, Agent, or Firm—Guido Modiano; Albert Josif

[57] ABSTRACT

A dilator for application in the medical field, comprises a hollow body made of an elastically deformable material and defining a cavity. Ducts hydropneumatically connect the cavity of the body to a source of pressurized fluid, valves controlling the hydropneumatical communication between the cavity and the source of pressure fluid and the outside. The body expands when positioned in situ and when in hydropneumatic communication with the source of pressurized fluid and being thereby effective to dilate the corporeal application field.

4 Claims, 8 Drawing Figures

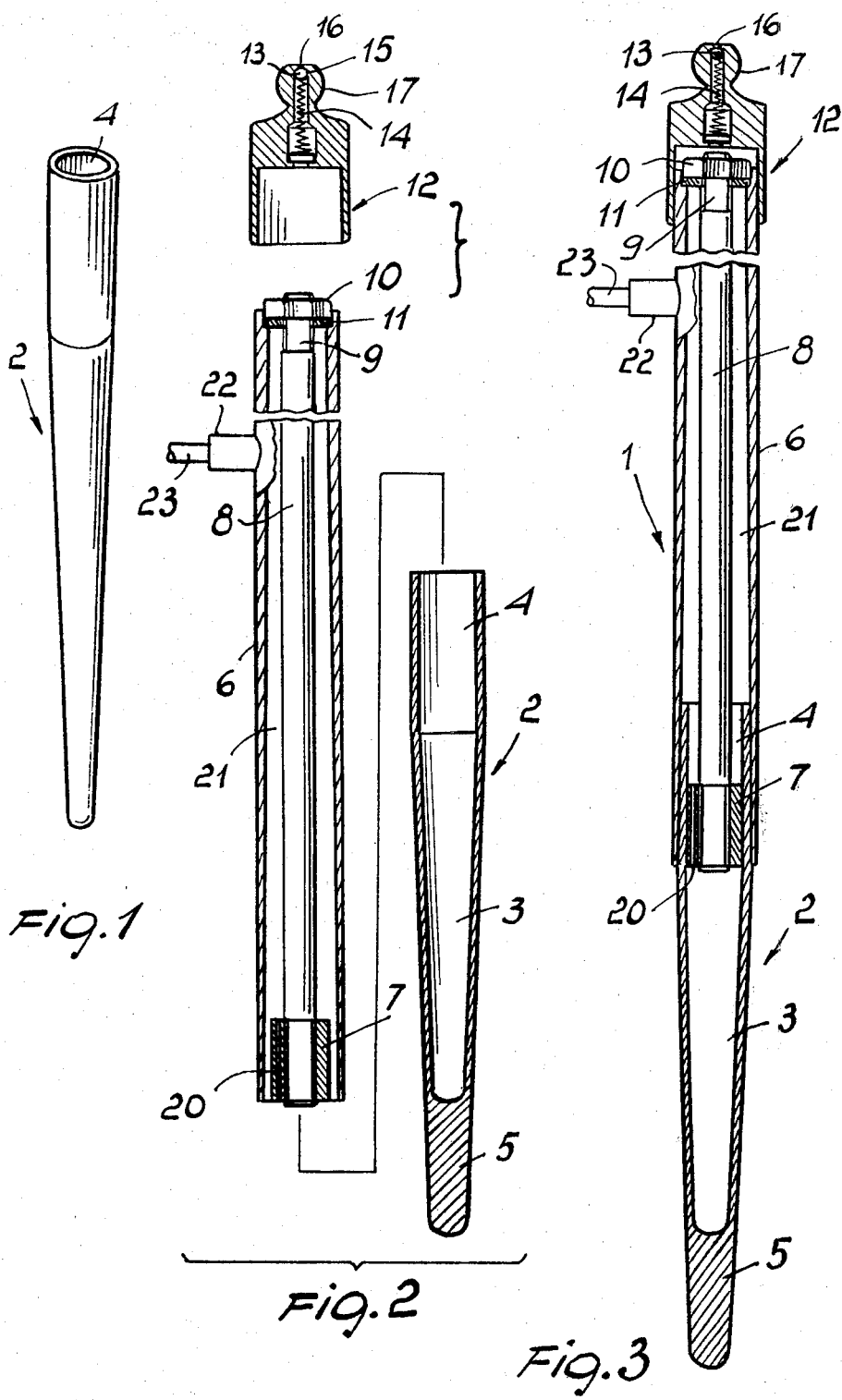

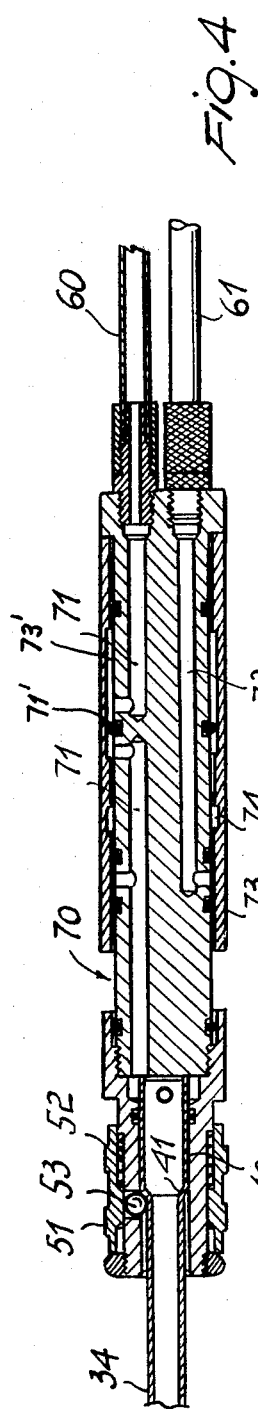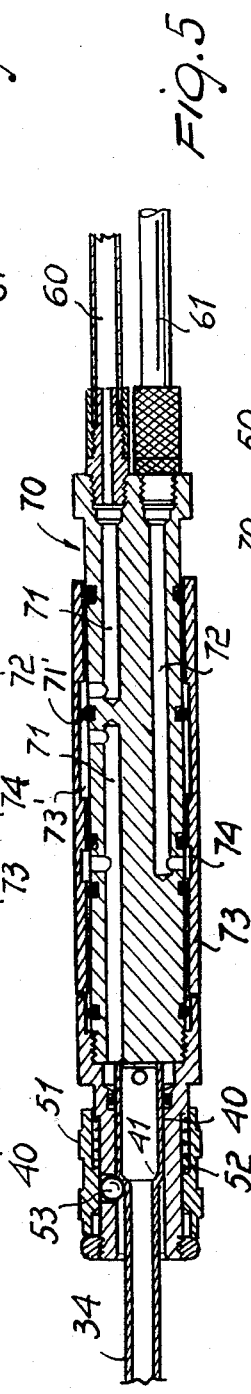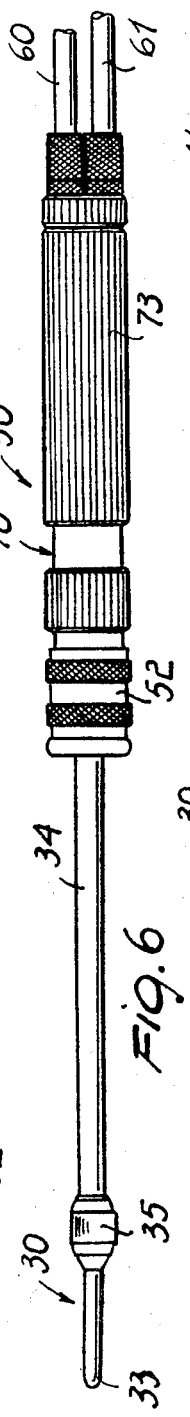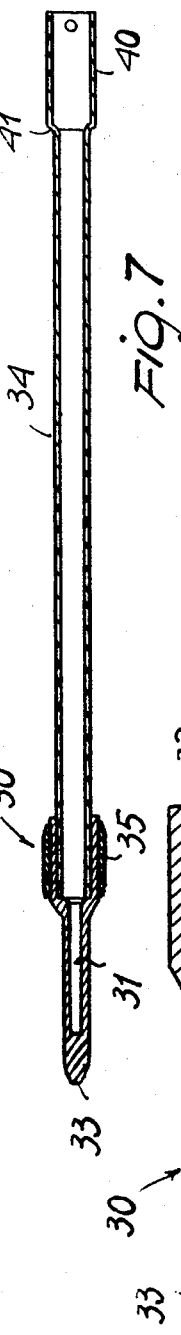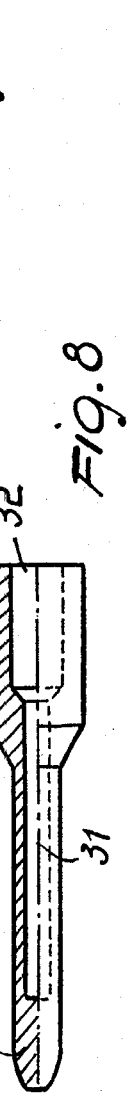

DILATOR FOR APPLICATION IN MEDICAL FIELD

BACKGROUND OF THE INVENTION

This invention relates to a dilator for application in the medical field.

As is known in the medical art, it is often necessary to dilate a surgical area.

To just review but a few exemplary cases, it happens in urology, and more specifically with urethral and ureteric lithiasis, that the presence of calculus requires dilation in order to facilitate the intervention and the expulsion of the calculous formation. Currently, in such cases as this, recourse is generally made either to a pharmacological therapy, with only moderately successful results, as the experts will recognize, or a set of catheters, made of metal or other materials, are employed which have gradually increasing diameters, such as to crush the calculous formation, or eventually surgical intervention is resorted to.

The introduction of catheters of gradually increasing sizes requires first of all considerable skill of the physician, while much time is required to achieve the desired dilation of the part.

A similar problem is encountered in obstetrics, where the obstetrician daily finds it necessary to dilate the uterine neck as a matter of routine.

To produce the cited dilation, several methods are known in the medical art, among which the laminae vegetales (still used, although infrequently), Champetier De Ribes's bladder, various dilators by now abandoned, and the Hegar dilators, the only ones left in this field.

The Hegar dilators are metal cones of progressively larger diameters, which are first introduced, left in situ for a while, and then extracted before applying higher diameter ones.

The results to be obtained with the cited dilators are good, provided that they are handled by a skilled hand, to avoid the risks of perforation and/or laceration as is the case whenever an object is introduced in tender parts of the human body.

The above merely reflects some examples of how frequently, in the various specializations, a physician is called upon to dilate tender parts of the human body by means which are not always entirely satisfactory, since they all exhibit limitations, potential hazards, and occasionally even applicational difficulties of a practical nature.

SUMMARY OF THE INVENTION

Thus, it is an object of this invention to eliminate the limitations mentioned above, by providing a dilator for medical applications, which while combining all of the advantages afforded by the prior art devices, is adapted to remove all the hazards normally connected with the use of conventional devices as described above.

Another object of this invention is to provide a dilator as indicated, which may be utilized in several different applications of the medical art, in correspondingly different configurations thereof, and in practice applied to all those situations which require dilation of a tender part of the human body.

It is a further object of the invention to provide a dilator which is constructed such as to afford the desired result in a remarkably shorter time and which, moreover, affords the possibility of carrying out the dilation continuously.

Still another object of the invention is to provide a dilator which is quickly adaptable for individual applicational requirements, inasmuch as it can easily assume any desired size.

A not unimportant object of this invention is to provide a dilator which can be easily constructed of elements and materials commonly available on the market, and which is also capable of affording maximum reliability and safety.

These and other objects, such as will be apparent hereinafter, are achieved by a dilator for the application in medical field, characterized in that it comprises an at least partially hollow body made of an elastically deformable material and defining a cavity and having a distal and a proximal end thereof, duct means for hydropneumatically connecting the cavity of said body to a source of pressurized fluid, valve means for controlling the hydropneumatical communication between said cavity and said source and the outside, said body expanding when positioned in situ and when in hydropneumatic communication with said source of pressurized fluid and being thereby effective to dilate the corporeal application field.

BRIEF DESCRIPTION OF THE DRAWINGS

Further features and advantages will become more clearly apparent from a description of preferred, though not exclusive, embodiments of a dilator for application in the medical field, illustrated by way of example only in the accompanying drawings, where:

FIG. 1 shows schematically and in perspective the body made of a deformable material;

FIG. 2 shows the dilator in exploded view and longitudinal section;

FIG. 3 shows the dilator in longitudinal section;

FIGS. 4 and 5 show, in sectional views, the actuating body in two different operative positions.

FIG. 6 is a general view of another embodiment of the instant dilator;

FIG. 7 is a sectional view of a further embodiment of the elastically deformable body associated with the tubular duct; and FIG. 8 is a sectional view of the elastically deformable body of FIG. 7.

DESCRIPTION OF THE PREFERRED EMBODIMENTS

With reference to the cited drawing figures, the dilator for application in the medical field, according to this invention, which is indicated generally at 1, comprises a body 2 of an elastically deformable material. Said body 2 is composed of a sterile material having high properties of elasticity, hardness and resistance to tear, wear and aging, and has a substantially elongated, e.g. conical, shape to define therewithin a cavity, e.g. conical, indicated at 3. Moreover, it is provided at its major basis with a mouth 4, and at the opposite end, towards its tip, with a solid area 5 serving to strengthen the elastically deformable body and as a stiffening member for the body 2, such as to facilitate its introduction and penetration in situ.

Said body 2 can be connected to a pressurized fluid source through an outer tubular member 6, wherewith the body 2 is associated in tight sealed relationship through a tapering ring 7, which by engaging with the wall defining the opening 4 in the body 2 firmly secures the body 2 to one end of the tubular member 6.

Said tapering ring 7 is provided at the end of an inner tubular member 8 which, at the other end, has a threaded length 9 wherewith a nut 10 engages rotatorily, said nut acting, through a washer 11, on the end of the tubular member 6 such as to permit clamping of the tapering member 7 tightly; in practice the tubular member 8 acts as a tension rod for the tapered ring 7, thereby locking the body 2.

At the end of the tubular member 6 whereon the washer 11 is active, a closure cap 12 is provided which has internally located delivery valve means comprising a ball valve 13, biassed by a spring 14 toward a circular seat 15 formed with a bore 16. Furthermore, at the end of the cap where said hole 16 is located, the cap itself defines a projection 17 for connection to a delivery duct in communication with an electric pump.

Moreover, said tapering ring 7 is formed with a duct system 20 which communicates the cavity 3 of the body 2 to the interspace 21 defined between the outer tubular member 6 and the inner tubular member 8. Said interspace communicates, through discharge valve means 22, with an outlet or discharge duct 23 for the pressurized fluid (not further explained because known per se).

The dilator 1 is inserted in a pistol grip or handle which is connected, by means of a delivery pipe and return pipe, to an electric pump located in a specially provided unit. Said electric pump supplies of preference a distilled solution which is admitted to the dilator 1 through the bore 16 under control by the ball valve 13, then passed through the cavity provided in the tubular member 8, and reaches the inside of the elastically deformable body 2.

The elastically deformable body 2 expands evenly under control by the physician who is thus enabled to control and adjust gradually the amount and rate of such expansion according to necessity, such as to perform the dilation operation in a simple, effective, safe and painless manner.

The body 2, owing also to its preferably conical shape, can be easily introduced into the part to be dilated, obviously prior to the admission of pressurized fluid to its interior, and can be held at the selected point as long as required, while the desired dilation is achieved by controlling the pressure level of the fluid admitted from the electric pump.

Upon reaching the desired dilation, which occurs while the cited discharge valve means are closed, the fluid from the elastically deformable body 2, which passes through the duct system or channel 20 and the interspace 21, is led out through the discharge valve 22 when the latter is opened by hand thereby to cause the body 2 to recover its original size for easier extraction.

According to another embodiment of the invention, the dilator comprises an elongate body 30 of an elastically deformable material, said body 30, which is made of a sterile material having high elasticity, hardness, and wear and tear resistance properties, defining a cavity 31 therein; said cavity 31 has at a proximal end thereof an open portion 32, whereas the distal end has a solid portion 33 serving to strengthen the elastically deformable body and as a stiffening member for the body 30, such as to facilitate the introduction and penetration thereof in situ.

The body 30 is sealingly associable with the end of a tubular duct 34, specifically the end of the tubular duct 34 is inserted into the open portion 32 and the sealing action is provided with a shape 35 clamping the body 30 tight onto the end of the tubular duct 34, which is made of a substantially rigid material.

The tubular duct 34 communicates with the cavity 31 and defines, at its end remote from that connected to the body 30, a larger diameter portion 40 extending into the tubular duct through a conical shoulder 41 to afford connection of the tubular duct 34, through quick release latching means to be described hereinafter, to an actuating body 50.

The quick release latching means, known per se, comprise a sleeve 51 slidably mounted on the body 50 against the bias of a spring 52 and having internal cam surfaces for, up in axial movement thereof, selectively moving in a radial direction a small ball 53 adapted for engaging with the conical shoulder 41 such as to removably lock the tubular duct 34 with respect to the body 50.

The body 50 is effective to communicate the tubular duct 34 with a delivery duct 60 and discharge duct 61, which are controlled by a slide distributor 70 defined within the body 50. More precisely, the slide distributor has a delivery canalization 71 in permanent communication with the delivery duct 60 and tubular duct 34, the "O"-ring gasket 71' allowing fluid passage therethrough when facing the recess 73' of the slide 73.

The distributor 70 also comprises a discharge canalization 72 permanent communication with the discharge duct 61 and having its internal aperture controlled by a slide 73 which can move slidably on the distributor 70 from a first position where it blocks the communication between the delivery duct and discharge duct to a second position where an annular chamber 74 puts the delivery canalization 71 in communication with the discharge canalization 72 (FIGS. 4 and 5, respectively).

For a more complete description of the apparatus, it should be added that the delivery duct is connected to an electric pump which is effective to admit a sterile solution to the inside of the dilator, thus affording a uniform and elastic dilation, under control by the physician, of the body 30 at an expansion rate which is controllable and adjustable at will.

Furthermore, during the initial application step, it is advisable to put the delivery duct in communication with the discharge duct such as to perform in practice a flushing step in order to remove from the inside of the tubular duct 34 and deformable body 30 any air or similar residues. Thereafter, the discharge canalization is closed and dilation is carried out in the desired manner, while by re-opening the communication from the delivery canalization to the discharge one, the deformable body will contract elastically as gradually as desired.

Thus, it will be apparent that the invention, in this further embodiment thereof, affords an extremely simple form of connection between the deformable body 30 and actuating body 50, which simple connection capability is due to the body 30 being previously connected to a rigid tubular duct which can be coupled to the actuating body by quick release latching means.

From the foregoing description, it will be apparent that the invention achieves its objects, and particularly significant is the fact that the instant dilator is extremely safe, inasmuch as it cannot produce perforations, nor lacerations, it being made of an elastic material, and moreover it permits the part to be dilated for enlarging the surgical field continuously, that is the dimensions of the body 2 can be increased continuously, whereas in the prior art devices one hand to extract one body and insert a larger size one.

Another interesting aspect of the dilator described herein is that, by virtue of its varying the shape of the body 2, or of the body 30, the instant dilator may be utilized in several different medical applications, since the inventive concept and its design provide for its quick adaptation to various fields.

The invention as described hereinabove is susceptible to many modifications and variations which are all intended to fall within the scope of this inventive concept.

Furthermore, any of the details thereof can be replaced with other, technically equivalent elements.

In practicing the invention, the materials employed, provided of course that they are compatible with the intended use of the dilator, as well as the shape and dimensions may be any ones to meet individual applicational requirements.

With regard to the dilator embodiment shown in FIG. 2 it will be understood that the taper of the ring 7 is directed upwards i.e. with the reduced diameter portion facing towards the nut 10 so that initially the tapering ring is moved to project outwards from the opening end of the tubular member 6 to allow the proximal end of the body 2 to be pulled thereover. In order to lock the body 2 on the tubular member 6 it is sufficient to urge the tapering ring 7 towards the interior of the tubular member 6 by acting on the nut 10.

As above specified the material of which the dilator body proper is made will have to have the above specified properties. In practice good results may be obtained with silicon elastomers such as silicon rubber. Good results have been obtained with a material known under the commercial name "Silopren" and manufactured by the Bayer of West Germany. Other material may also be used.

The shape and dimensions of the dilator body proper may be of any kind suitable for the intended application. In case of application for uterine neck the diameter of the embodiment of cylindrical shape of the dilator body was 4 mm in non expanded condition, whereas in the inflated condition the diameter may reach 16 mm with an elongation of about 3.5 to 6 mm, with a length of the cavity of 25 mm, a length of the solid part of the distal end of 8 mm and a length of the proximal socket like end portion of about 14 mm, the total length being about 45 mm. For other applications a diameter of 10 mm with a possibility of expansion to about 25 mm was found appropriate. Other dimensions may be appropriate for other applications. The cylindrical embodiment of the dilator body shown in FIG. 8 assumes in inflated condition a shape which in the central part of the cavity remains cylindrical with an increased diameter, while near the distal and proximal ends of the body the cylindrical shape gradually tapers towards the initial non inflated diameter. In some particular applications a spherical shape of the dilator body either in non inflated or in inflated condition may be appropriate. It has been found convenient to use a diameter under non inflated condition which is slightly less than the diameter of the aperture in which the dilator has to be inserted, in order to reduce to a minimum the resistance to penetration of the dilator body thereby to avoid bending of the walls thereof surrounding the cavity.

It has been found appropriate to use for the fluid under pressure a liquid suitable for the anatomic organ to be dilated. Such for example, for uterine applications a liquid manufactured by the Swiss Company Geigy and known under the commercial name "Bactofen" was used. Antioxidant substances may be added to such liquid if desired in small proportions to avoid oxidation of component parts of the dilator. It was found that an appropriate pressure for the dilator is of about 6 to 10 kg/cm$^2$, with a wall thickness of the dilator cavity of about 1.25 mm.

We claim:

1. A dilator for the application in medical field, comprising an at least partially hollow body made of an elastically deformable material and defining a cavity and having a distal and a proximal end thereof, duct means for hydropneumatically connecting the cavity of said body to a source of pressurized fluid, valve means for controlling the hydropneumatical communication between said cavity and said source and the outside, said body expanding when positioned in situ and when in hydropneumatic communication with said source of pressurized fluid and being thereby effective to dilate the corporeal application field and wherein said hollow body is an elongated body, said duct means include a substantially rigid tubular duct sealingly connected with one end thereof to said proximal end of said body, a control body connected to the other end of said substantially rigid tubular duct, quick release latching means for maintaining the connection between said control body and said substantially rigid tubular duct, said control body having connected therewith an inlet duct for the fluid under pressure and an outlet duct therefor and a slide distributor controlling the flow of pressurized liquid therethrough.

2. A dilator according to claim 1, characterized in that it comprises an annular clamping strap for providing connection between said substantially rigid tubular duct and said proximal end of said dilator body.

3. A dilator according to claim 1, characterized in that said tubular duct has at the end thereof remote from the end connected to said body an embossment connected to said tubular duct through a conical shoulder wherein a ball actuated by said quick release latching means is adapted to engage for connection.

4. A dilator according to claim 1, characterized in that said slide distributor defines a delivery canalization therein in communication with said inlet duct and said tubular duct, as well as a discharge canalization in communication with said outlet duct, there being further provided a slide member movable from a first position where said slide member blocks the communication between said delivery canalization and said discharge canalization, to a second position where said slide member puts said delivery canalization into communication with said discharge canalization, and viceversa.

* * * * *